United States Patent [19]

Lavretskaya et al.

[11] Patent Number: 4,550,113
[45] Date of Patent: Oct. 29, 1985

[54] 9-AMINO-2,3,5,6,7,8-HEXAHYDRO-1H-CYCLOPENTA(B)QUINOLINE MONOHYDRATE HYDROCHLORIDE AS STIMULANT OF NEURO-MUSCULAR TRANSMISSION OF SMOOTH MUSCLES

[75] Inventors: Elionora F. Lavretskaya, Moscow; Ernest A. Rudzit, Moskovskaya; Lev A. Piruzian, Moscow; Ljubov I. Volkova, Moskovskaya; Nina I. Zakharova, Moscow; David A. Sarkisian; Alexandra V. Upadysheva, both of Moskovskaya; Natalya D. Grigorieva, Moscow; Anna P. Znamenskaya, Moscow; Rakhil E. Libinzon, Moscow; Semen G. Antonian, Moscow, all of U.S.S.R.

[73] Assignee: Nauchno-Issledovatelsky Institut Po Biologicheskikm Ispytaniyam Khimicheskikh Soedineny, Kirova, U.S.S.R.

[21] Appl. No.: 577,304

[22] Filed: Feb. 6, 1984

Related U.S. Application Data

[63] Continuation of Ser. No. 409,606, Aug. 19, 1982, abandoned.

[51] Int. Cl.[4] .................... A61K 31/47; C07D 221/16
[52] U.S. Cl. .................................. 514/290; 260/464; 546/79
[58] Field of Search ................... 424/258; 546/79; 514/290

[56] References Cited

PUBLICATIONS

Upadysheva, A., et al., *Pharm. Chem. J.*, 11(2), 184 (1977).
Upadysheva, A., et al., *Khim. Geterosikl. Soedin.* 1983, (1), 107-111.
*Chemical Abstracts*, 86: 189676q (1977) [Upadysheva et al., *Khim.-Farm. Zh.* 1977, 11(2), 40-44].
*Chemical Abstracts*, 87: 531135 (1977) [Upadysheva et al., U.S.S.R. 552, 328, 3/30/77].
*Chemical Abstracts*, 88: 105251c (1978) [Upadysheva et al., *Khim. Geterosikl. Soedin.* 1977, (11), 1549-1553].
*Chemical Abstracts*, 97: 216034q (1982) [Grigor'eva et al., U.S.S.R. 615, 653, 5/7/82].
Patnaik, G., et al., *J. Med. Chem.*, 9, 483-488 (1966).

*Primary Examiner*—Richard A. Schwartz
*Attorney, Agent, or Firm*—Burgess, Ryan & Wayne

[57] ABSTRACT

A novel compound and composition are disclosed which stimulate neuro-muscular transmission of smooth muscles and cause excitation of conductance in the peripheral and central nervous systems, comprising the active ingredient - 9-amino-2,3,5,6,7,8-hexahydro-1H-cyclopenta(b)quinoline monohydrate hydrochloride of the general formula:

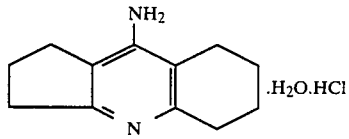

and a pharmaceutical carrier.

9 Claims, No Drawings

9-AMINO-2,3,5,6,7,8-HEXAHYDRO-1H-CYCLOPENTA(B)QUINOLINE MONOHYDRATE HYDROCHLORIDE AS STIMULANT OF NEURO-MUSCULAR TRANSMISSION OF SMOOTH MUSCLES

This application is a continuation, of application Ser. No. 409,606, filed Aug. 19, 1982, now abandoned.

FIELD OF THE INVENTION

The present invention relates to a medicine, and more specifically, to a novel compound and composition which stimulates neuro-muscular transmission of smooth muscles and causes excitation in the peripheral and central nervous systems which is useful in the treatment of various injuries of the peripheral nervous system with motor disturbances (neuritides, polyneuritides, polyradiculoneuritides), for the treatment of post-effects of the previously incurred vascular injuries of the brain; myasthenia or other neuro-muscular diseases which are inherited; for stimulation of delivery in birth, for the treatment of patients with atony and akinesia of the gastro-intestinal tract and the like.

BACKGROUND OF THE INVENTION

Known in the art are medicated compounds which stimulate neuro-muscular transmission, which are reversible-effect cholinesterase inhibitors such as proserin (neostygmin), galantamine (nivalin), oxazyl (Ambenonium chlorobenzylchloride). However, these prior art preparations have a short-time and insufficient therapeutic effect and a high toxicity ($LD_{50}$ of galantamine subcutaneously injected in mice is 14 mg/kg, intraperitoneally administered—11 mg/kg; $LD_{50}$ of hypodermally injected proserin is 0.4 mg/kg).

Moreover, galantamine is produced from a particular variety of snowdrop flowers (*Galanthus woronowi A. Los.*) which makes it expensive and not readily available.

SUMMARY OF THE INVENTION

It is the main object of the present invention to provide a novel compound and composition which (a) stimulates neuro-muscular transmission of smooth muscles and improves excitation in the peripheral and central nervous systems (b) possesses low toxicity, and (c) combines the inhibition of cholinesterase with the blocking of potassium channels of the excitable membranes and thus extend the action potentials.

The compound and composition according to the present invention is novel and hitherto unknown in the literature.

The novel medicated composition which stimulates neuro-muscular transmission of smooth muscles and improves excitation conductance in the peripheral and central nervous systems comprises, according to the present invention, the active ingredient 9-amino-2,3,5,6,7,8-hexahydro-1H-cyclopenta(b)quinoline monohydrate hydrochloride of the formula:

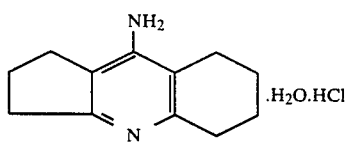

The composition according to the present invention is preferably employed as injection solutions and in tablets. The composition according to the present invention in the form of injection solutions preferably contains the active ingredient in the amount of 1.5% by weight and, as the pharmaceutical carrier, bidistilled water acidified to a pH of from 3.5 to 5.0.

The composition according to the present invention in the form of tablets preferably contains the active ingredient in an amount of from 15 to 30 mg. As the pharmaceutical carrier for the tablets it preferably contains starch or sugar powder.

DETAILED DESCRIPTION OF THE INVENTION

The medicated composition according to the present invention has a new type of pharmacological activity, the main manifestation of which is stimulation of the neuro-muscular transmission, enhancement of excitation in excitable tissues (nerve, smooth and striated muscles), as well as restoration of conductance in nerves, neuro-muscular synapses in the case of injury thereof.

Special experimental investigations have shown that the active ingredient of this action of the composition according to the present invention is based on a combination of effects at the molecular level: (1) it blocks the potassium channels of the excitable membranes and (2) it inhibits the cholinesterase.

The composition according to the present invention is useful for the treatment of various injuries of the peripheral nervous system (neuritides, polyneuritides, polyradiculoneutides). It has a superior therapeutic effect over all other medicated compounds including known inhibitors of cholinesterase such as proserin, galantamine, oxazyl. Restoration of the nerve function is observed even during distant periods of the disease where no other kinds of treatment provide any therapeutic effect.

Especially good therapeutic results are obtained in the case of treatment of neuritis of the facial nerve where the composition according to this invention provides its effect even in the presence of contracture. Due to the analgesic properties of the preparation it exerts a combined positive effect in the case of radiculitis and radiculoneuritides: it removes the pain syndrome and restores functions of the neuro-muscular synapses.

A positive, though less pronounced, effect is revealed by the composition according to the present invention in the case of myasthenia, hereditary neuro-muscular diseases, and disseminated sclerosis. It results in a certain improvement also during the rehabilitation period after insults, operations of aneurysms of brain vessels. The composition substantially improves the memory of patients suffering from cerebral atherosclerosis, with post-effect of skull traumata and the like. The composition is also indicated for the treatment of intestinal atonia, urinary bladder atonia, weak labor activity, as well as certain forms of impotentia.

The medicated composition according to the present invention has been experimentally tested on animals and in clinics on patients suffering from various kinds of pathology.

Thus, there has been studied the effect of the medicated composition of the present invention on neuro-muscular transmission in experiments on a rat's phrenico-diaphragmatic preparation, musculus rectus abdominis of the frog, and rabbit's sciatic nerve.

Experiments are carried out on phrenico-diaphragmal preparations obtained from male rats weighing 200 g. From the diaphragm two muscular strips are cut of 5-8 mm width with appropriate nerves of 20 mm length. The preparation is placed into a bath with an aerated Tyrode solution with a double content of glucose at a temperature of 20° C., and the pH of the solution is brought to 7.3. The nerve is placed on two silver electrodes through which the muscle preparation is stimulated.

The stimulation parameters are square pulses with a duration of 1 msec, groups of 10 pulses with an interval of 2 seconds therebetween and 1 minute intervals between the groups at a voltage of 12-15 V.

The experiments have shown that the addition to the bath, of the medicated composition according to the present invention at a concentration of $1.10^{-7}M$ causes an increase in the amplitude of the diaphragm contractions by 74-80%. This increase slowly declines after the removal of the composition from the solution, but even one hour after the washing-off the contraction still remains increased by 25%.

In a similar concentration galantamine provides an increase in the amplitude of 28%, its effect is but short-termed and disappears 20 minutes after the beginning of washing.

The cut musculus rectus of a frog's abdomen is placed into a vessel with Ringer solution (pH=7.4) through which air is passed. The muscle contractions are recorded by a strain gauge. Acetylcholine is introduced into the solution to obtain a final concentration of $1.10^{-6}M$. The preparation is introduced into the solution to a final concentration within the range of from $1.10^{-7}$ to $1.10^{-6}M$. Against the background of the composition of the present invention acetylcholine causes a contraction which is superior to the control by 180%. The effect occurs within 10-15 minutes and slowly diminishes upon the removal of the composition from the solution. 25 minutes after the removal the response to acetylcholine is still equal to 150% vs. the control value.

Under the same conditions, galantamine and proserin give less pronounced and shorter enhancement of the effect of acetylcholine.

In experiments on a rabbit's sciatic nerve (in situ), the composition according to the present invention increases the amplitude of contractions of the musculus gastrocnemius by 50-78% in response to the addition of acetylcholine. The effect is long lasting: it is still observed one hour after addition of the composition according to the present invention.

The effect on miniature end plate potentials (EPP) has been studied on neuro-muscular synapses (n.peroneusm.extensor digitorumlongus). Mice are given the composition of the present invention in doses of from 5.2 to 10.4 mg/kg (10-20% of $LD_{50}$) and then are slaughtered within different time limits after the injection, a neuro-muscular preparation is isolated and miniature EPP are studied.

The following parameters of the end plate potentials are measured: frequency (f), amplitude (A) and duration (t).

In the control preparations the parameters of miniature end plate potentials are as follows: f=3.0 1/sec, A=0.6 mV, t=0.3 msec. Upon the addition of the composition according to the present invention in the concentration of $10^{-6}M$ the parameters are changed: f=3.0 1/sec, A=1.2 mV, t=7.0 msec.

Therefore, there is observed an increase of the amplitude and duration of miniature EPP. This effect is but of short duration and it is detected only in preparations isolated within 30 minutes after the addition of the composition.

The composition according to the present invention weakens the effect of myorelaxants of the curare-type, in particular d-tubocurarine. It lowers toxicity of the latter. Thus, in experiments on mice there are determined medium lethal doses of d-tubocurarine in control and test groups which have been previously administered with the medicated composition of the present invention. $LD_{50}$ of myorelaxant is increased from 0.29 mg/kg to 0.69 mg/kg.

Tubocurarine in a dose of 0.25 mg/kg administered intravenously results in head drop in rabbits due to blocking of neuro-muscular transmission. Injection of the composition of this invention intravenously in doses of 1.3, 2.6, 5.2 mg/kg after registration of the symptom results in recovery of the muscular tension. The anticuraric effect lasts 30 to 40 minutes.

The effect of the composition according to the present invention on smooth-muscle objects has been studied in experiments on uterus, vas deferens and the intestine of rats. Animals are slaughtered by decapitation, the peritoneal cavity is opened, the smooth-muscle organ is cut out and transferred into a vessel containing a physiological solution. A strip of 15×2 mm is cut from the organ, silk threads are secured to the strip ends and the muscle preparation is placed into a testing unit chamber. The contractile activity of the muscle is recorded under isometric conditions by means of a tensometer. The muscle is in a continuous flow of an aerated physiological solution. Spontaneous contractions are recorded and contractive responses to agonists (acetylcholine, oxytocin, adrenalin, serotonine, histamine, KCl). The composition according to the present invention, while enhancing the responses, increases the amplitude of contractions in response to all agonists, except $K^+$. The conventional inhibitors of cholinesterase do not possess such an effect, they merely slightly increase the response of uterus to the action of acetylcholine.

The stimulating effect of the composition according to the present invention is also lasting and detected 40 minutes after its removal from the solution.

In experiments on rat's sciatic nerve placed in a special chamber, there has been studied the effect of the composition according to the present invention on the conductivity of excitation. Pulses are passed through a stimulant electrode and the second recording electrode registers the nerve action potentials in response to excitations.

The composition is applied in a concentration of from $1.10^{-5}$ to $1.10^{-7}M$ onto a limited length of the nerve between the electrodes. KCl in a concentration of $5.10^{-5}M$ causes blocking of the conductivity. The compound according to the present invention removes this blocking and restores the conductivity of the nerve.

The experimental studies have shown that the composition according to the present invention has two groups of effects: a short (30 minutes maximum) effect which is due to inhibition of cholinesterase; and a long-time effect which can be explained by a direct effect on muscular and nervous fibres. The composition of the present invention has similar features and clear-cut distinctions as compared to conventional cholinesterase inhibitors such as galantamine and proserin.

In contrast to the latter agents, it demonstrates a more pronounced effect on neuro-muscular transmission, stimulates smooth muscles and enhances the effects of all agonists except $K^+$. It restores conductivity of excitation in the nerve after blockage with KCl.

In experiments on purified preparation soft brain acetylcholinesterase (ACE) and serum butyrylcholinesterase (BuCE) it has been shown that the composition according to the present invention is superior to galantamine and approaches proserin as regards the intensity of the inhibiting effect.

Its inhibition constant $K_i$ relative to ACE is $1.47 \times 10^{-7} M$, relative to BuCE—$5.6 \times 10^{-9} M$. The compound inhibits ACE in a combined manner, BuCE—in a non-competitive manner.

For galantamine $K_i$ are equal respectively to $2.5 \times 10^{-6} M$ (ACE) and $1.6 \times 10^{-4} M$ (BuCE); for proserin—$6.5 \times 10^{-8} M$ (ACE) and $1.5 \times 10^{-7} M$ (BuCE).

The composition according to the present invention in the concentration of $1.10^{-6}$ to $1.10^{-5} M$ effectively blocks potassium currents in an electroexcitable membrane by 50–70%. This effect is characteristic of a known inhibitor of potassium channels of the membrane—4-aminopyridine. However, upon prolonging the test voltage pulse from 10 msec to 1 sec, the inhibition of $K^+$ current by 4-aminopyridine disappears, while the effect of the composition according to the present invention is fully retained. Without fixation of the potential the composition causes a pronounced extension of the potential of the membrane effect.

In experiments on mice, rats, rabbits and dogs there has been studied the influence of the composition according to the present invention of the behavior, electroencephalogram, training; effects of combination with somnific agents, arecoline, nicotine, apomorphine, phenamine, L-DOFA, 5-hydroxytryptophan. In small doses it does not change the animal behavior. In doses of from 10 to 20 mg/kg, it reveals a stimulating effect on the central nervous system, enhances activity, and responses to irritations. In higher doses, there is observed excitation of animals, tremor, signs of stimulation of M-cholinergic systems: hypersalivation, hyperperspiration, and diarrhea. In toxic doses convulsions are developed.

The composition according to the present invention potentiates the effects of arecoline. The effect of apomorphine, phenamine and L-DOFA are enhanced by the composition of the present invention only in high doses thereof (from 10.4 to 20.8 mg/kg).

It facilitates training of rats in a T-shaped labyrinth.

Therefore, the experimental data have shown that the composition according to the present invention possesses all of the effects characteristic of inhibitors of cholinesterase. But, in addition thereto, it possesses a number of properties which has not been described for any other anticholinesterase agent, namely:

A lasting, direct stimulant effect on muscles; ability of restoring and stimulating conduction of excitation in a nerve.

The present invention for the first time provides a composition with its spectrum of action combining inhibition of cholinesterase and blocking of potassium channels of the membrane. This combination of properties makes especially effective the influence of the composition on conduction of excitation. In this case it acts on all units taking part in the conduction: presynaptic fibre→release of the mediator→blocking of enzymatic decomposition of the mediator in the synapse→effect on post-synaptic nervous or muscular fibre.

There was carried out the study of an acute and chronic toxicity of the composition according to the present invention.

The $LD_{50}$ upon single intraperitoneal administration to mice is 44 mg/kg, hypodermally—52 mg/kg, per os—68 mg/kg, to rats hypodermally—60 mg/kg.

Chronic toxicity of the composition has been studied on three kinds of animals (rats, dogs, rabbits). In chronic experiments on these kinds of animals there has been studied the effect of a lasting hypodermal administration of the composition on the general health condition and bodyweight of the animals, hemogram, cardiovascular system, respiration, central nervous system, functional state of kidneys, liver, and thyroid gland. From the results obtained and from the morphological investigation, it has been found that upon a long-time course of administration (rats—3 months, rabbits—2 months, dogs—6 months), the composition does not provide any toxic effect on laboratory animals. The dose employed in the experiments with the composition of the present invention exceeded that required for a human being (per kg of bodyweight) by 5–10 times.

Tests also have been carried out to evaluate allergogenic activity of the composition according to the present invention. The test results demonstrate that the composition has no allergogenic effect.

The compound reveals neither carcinogenic, mutagenous, teratogenous or embryotoxic effects.

The composition of the present invention has been tested in clinics of neurological and therapeutic profile; there were treated 550 patients with different forms of pathology.

The composition was administered to patients with injuries of the peripheral nervous system and locomotive disturbances: neuritides, polyneuritides, polyradiculoneuritides; with post-effects after previous vascular injuries of brain vessels, after certain operations on brain menigeomas, myasthenia and other neuro-muscular diseases which are inherited or of acquired genesis; for stimulation of delivery activity, for the treatment of patients with atony and akinesia of the gastrointestinal tract.

Indications for administration of the composition according to the present invention are substantially wider, but during the period of clinical studies it has been employed only for the main forms of pathology for which manifestation of the maximum therapeutic effect was expected.

Given hereinbelow are the results of analysis of efficiency of the preparation carried out on 320 patients (210 men and 110 women aged 20 to 61 years).

As to the forms of pathology, the patients were classified as follows:
 neuritides: 70 patients;
 polyneuritides: 20 patients;
 polyradiculoneuritides: 15 patients;
 discogenous radiculoneuritis: 40 patients
 myasthenia: 40 patients;
 post-effect of disturbed brain blood circulation: 50 patients;
 post-effects of neurosurgical operation of meningioma: 5 patients;
 disseminated sclerosis: 15 patients;
 amyotrophic lateral sclerosis: 10 patients;
 progressive muscular dystrophy: 20 patients;
 delivery stimulation: 30 patients;

intestine atony: 15 patients.

The composition of the present invention was administered to all patients as subcutaneous injections of a 0.5 or 1.5% solution. Single doses were varied from 10 to 30 mg, daily doses—from 10 to 60 mg. The duration of the therapeutic course depending on the character of diseases was varied from 10 to 30 days; in the case of myastenia it was even longer. The highest efficiency was noted in the case of injuries of the peripheral nervous system. The best effect was observed in patients with neuritides and polyneuritides of infectional and traumatic etiology (88% of improvement); somewhat less is the effect in radiculoneuritides of the discogenous origin (62% of improvement). Positive dynamics of neurological symptomatics in these patients revealed itself in greater scale of active movement, increased muscular power in injured groups of muscles, more vivid tendinous responses, recovery of sensitivity, disappearance of the pain syndrome (in this case the composition of the present invention also reveals analgetic properties). A good effectiveness should be noted in the case of treatment of patients suffering from peripheral paresis of the facial nerve. In this case the therapeutic effect was noted not only in fresh instances of the disease, but even at a long duration of the facial neuritis (1–3 years) after unsuccessful use of all kinds of pharmaceutical and physiotherapeutic treatment, including the use of anticholinesterase preparations. A successful result was obtained with the use of the composition of the present invention in the case of myastenia (92% of improvement). During the treatment of patients suffering from myasthenia it was found that the composition of the present invention had specific properties distinguishing it from such anticholinesterase preparations such as proserin, oxazyl. It ensures a therapeutic effect upon its lasting, course-scheduled administration; its effect is revealed not insomuch in a better synaptic transmission, but rather in the change of the contractibility of muscles, higher efficiency of muscular contractions. Improvement is noticed in patients suffering from disseminated sclerosis (60%), especially in patients with mild locomotory disturbances without pronounced and resistant paralysis. In the case of diseases of the central nervous system the treatment with the composition of the present invention has also proven effective, though not to the same extent as in the case of injuries of the peripheral nervous system. In patients with post-effect disturbances of brain blood circulation there has been observed amelioration of psychic functions, memory, and attention activity. In the case of pronounced locomotive and disphasia disturbances (deep paresis, paralysis, aphasia), the latter phenomena did not disappear, but there was noticed a certain improvement of brain functions, enlargement of communicative speech opportunities.

In the case of amyotrophic lateral sclerosis and neuromuscular dystrophia no effect was observed.

A specific positive effect of the composition according to the present invention was observed in the case of a weak delivering activity. 10 minutes after the administration of 10 mg of the composition there is observed an increasing contractive activity of uterus and development of a normal delivery, followed by normal birth without any complications (96% of the effect).

Positive results have been also noted in the case of diskinesia and atonia of intestine and bile ducts.

The composition according to the present invention is also distinguished by a good tolerance and rare side effects. It very rarely causes signs of M-cholinergic structures: intensified peristaltic of intestine, vomition, salivation (6 patients—1.8%). In contrast thereto, proserin causes these kinds of disturbances in 50% of patients and they are more significantly pronounced so that increasing doses of proserin in the case of its insufficient activity becomes impossible due to heavy manifestation and severity of side phenomena. The same relates, though to a lesser extent, to another anticholinesterase preparation—galantamine. In 4 patients (1.2% there was noted bradicardia, in 2—increase of arterial pressure (passing)—0.6%, in 4 patients (1.2%)—allergic dermal eruption rapidly disappearing after completion of the treatment course. Low frequency and weak manifestation of side effects, good tolerance of the preparation enable a broad variation of its single and daily doses and, when required, to considerably increase the same.

Therefore, the composition according to the present invention features a specific spectrum of its activity; it reveals a specific stimulating and recovering effect in the cases of injuries of peripheral, in particular skull-brain nerves where all known anticholinesterase preparations prove ineffective. It provides a direct action of muscles improving their contractive characteristics. The composition according to the present invention improves characteristics of the psychic activity, brain functioning during the recovery period after disturbances of the brain blood circulation, brain traumata, operations. It stimulates a weakened delivering activity, eliminates atonia of the gastro-intestinal tract.

The composition according to the present invention is preferably employed as injection solutions and tablets. The preparation is administered in doses of from 0.01 to 0.03 g as tablets twice a day; as 1.5% injection solutions 1–2 times a day.

The preparative forms of the composition according to the present invention are produced by conventional methods. The active principle—9-amino-2,3,5,6,7,8-hexahydro-1H-cyclopenta(b)quinoline monohydrate hydrochloride can be produced in the following preferred manner.

1-Amino-2-cyanocyclopentene-1, cyclohexanone, polyphosphoric acid and dry benzene are stirred upon boiling for two hours. After cooling the reaction mass is diluted with water and extracted with ether. The ethereal extract is discarded. The aqueous layer is neutralized to the pH of 7. The precipitate is filtered-off and several times washed with water on the filter. After separation of the precipitate the aqueous layer is combined with the washings and alkalinized with ammonia to a pH of 9–10. The resulting precipitate of 9-amino-2,3,5,6,7,8-hexahydro-1H-cyclopenta(b)quinoline is filtered-off and washed, then dissolved in 20 ml of ethanol and the ethanolic solution is treated by passing therein gaseous hydrogen chloride at a temperature within the range of from 5° to 25° C. to a pH of 3. The thus-obtained salt is precipitated by ethyl ether, the precipitate is reprecipitated from ethanol by ether. There is thus obtained 9-amino-2,3,5,6,7,8-hexahydro-1H-cyclopenta(b)quinoline monohydrate hydrochloride comprising a white or slightly creamy powder having no odor, readily soluble in water, slowly soluble in 95% ethanol, substantially insoluble in acetone, ether, chloroform, and readily soluble in diluted solutions of acids.

The composition according to the present invention pertains to the compounds of List A and should be stored in a light-protected place.

What is claimed is:

1. A pharmaceutical composition which blocks the potassium channels of the excitable membranes and inhibits choline esterase comprising an effective amount of 9-amino-2,3,5,6,7,8-hexahydro-1H-cyclopenta(b)quinoline monohydrate hydrochloride of the formula:

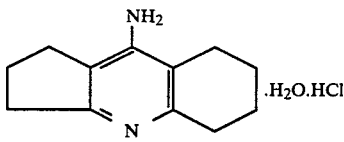

as the active ingredient and a pharmaceutical carrier.

2. The composition as claimed in claim 1 in the form of an injection solution containing 1.5% by weight of the active ingredient.

3. The composition as claimed in claim 2 wherein the carrier is bidistilled water acidified to a pH of from 3.5 to 5.0.

4. The composition as claimed in claim 1 in the form of tablets containing the active ingredient in an amount of from 15 to 30 mg.

5. The composition as claimed in claim 4, wherein said carrier is selected from the group consisting of starch and sugar powder.

6. A method for stimulating neuro-muscular transmission of smooth muscles and the peripheral and central nervous system in a warm blooded animal comprising administering to said animal an effective amount of the composition of claim 1.

7. The method of claim 6, further comprising administering said composition in the form of tablets containing between 0.01 and 0.03 gram of said active ingredient.

8. The method of claim 6, further comprising administering said composition in the form of an injectable solution containing between 0.5 and 1.5% of said active ingredient.

9. 9-amino-2,3,5,6,7,8-hexahydro-1H-cyclopenta(b)quinoline monohydrate hydrocholoride of the formula:

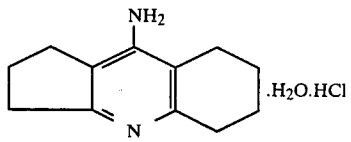

* * * * *